United States Patent [19]
Campoli

[11] Patent Number: 5,509,573
[45] Date of Patent: Apr. 23, 1996

[54] ASEPTIC DISPENSING SYSTEM

[76] Inventor: William J. Campoli, 16124 N. Point Rd., Huntersville, N.C. 28078

[21] Appl. No.: 216,683

[22] Filed: Mar. 23, 1994

[51] Int. Cl.$^6$ ........................... B65H 1/00
[52] U.S. Cl. ........................ 221/133; 221/277
[58] Field of Search ............... 221/75, 2, 3, 92, 221/124, 133, 130, 277

[56] References Cited

U.S. PATENT DOCUMENTS

| | | | |
|---|---|---|---|
| 3,441,174 | 4/1969 | Kenney | 221/75 |
| 3,989,163 | 11/1976 | Wittern | 221/75 |
| 4,032,039 | 6/1977 | Schuller | 221/133 |
| 4,240,563 | 12/1980 | Lennartson | 221/75 |
| 4,600,119 | 7/1986 | Olson | 221/197 |
| 4,664,289 | 5/1987 | Shimizu et al. | 221/2 |
| 4,744,490 | 5/1988 | Albright et al. | 221/75 |
| 4,757,915 | 7/1988 | Albright et al. | 221/75 |
| 4,844,294 | 7/1989 | Albright | 221/75 |
| 4,847,764 | 7/1989 | Halvorson | 364/413.02 |
| 4,869,395 | 9/1989 | Rubbmark | 221/131 |
| 4,986,441 | 1/1991 | Kanbe et al. | 221/130 |
| 5,091,713 | 2/1992 | Horne et al. | 340/541 |
| 5,197,632 | 3/1993 | Kaufman et al. | 221/197 |
| 5,205,436 | 4/1993 | Savage | 221/7 |

*Primary Examiner*—Kenneth Noland
*Attorney, Agent, or Firm*—Bell, Seltzer, Park & Gibson

[57] ABSTRACT

There is disclosed a system for maintaining and dispensing articles in an aseptic environment. The system includes a cabinet of modular units having at least one bank of shelves. Each bank has an open end and a closed end such that the open end is oriented toward a dispensing chute. Each bank contains a plurality of horizontally adjustable shelves laterally disposed in the bank. The shelves are divided by a plurality of dividers to define a series of slots on each shelf. A dispensing chute is located adjacent the open end of the bank and is adapted to provide gravity feed of an article. The articles are feed toward the dispensing chute by a feeding means such as an auger and the leading article is discharged by gravity. The operation of the feed means is controlled by a microprocessor or the like to control the delivery of articles to the dispensing chute. There is also disclosed a prepackaged cartridge of articles for use in the dispensing system.

28 Claims, 4 Drawing Sheets

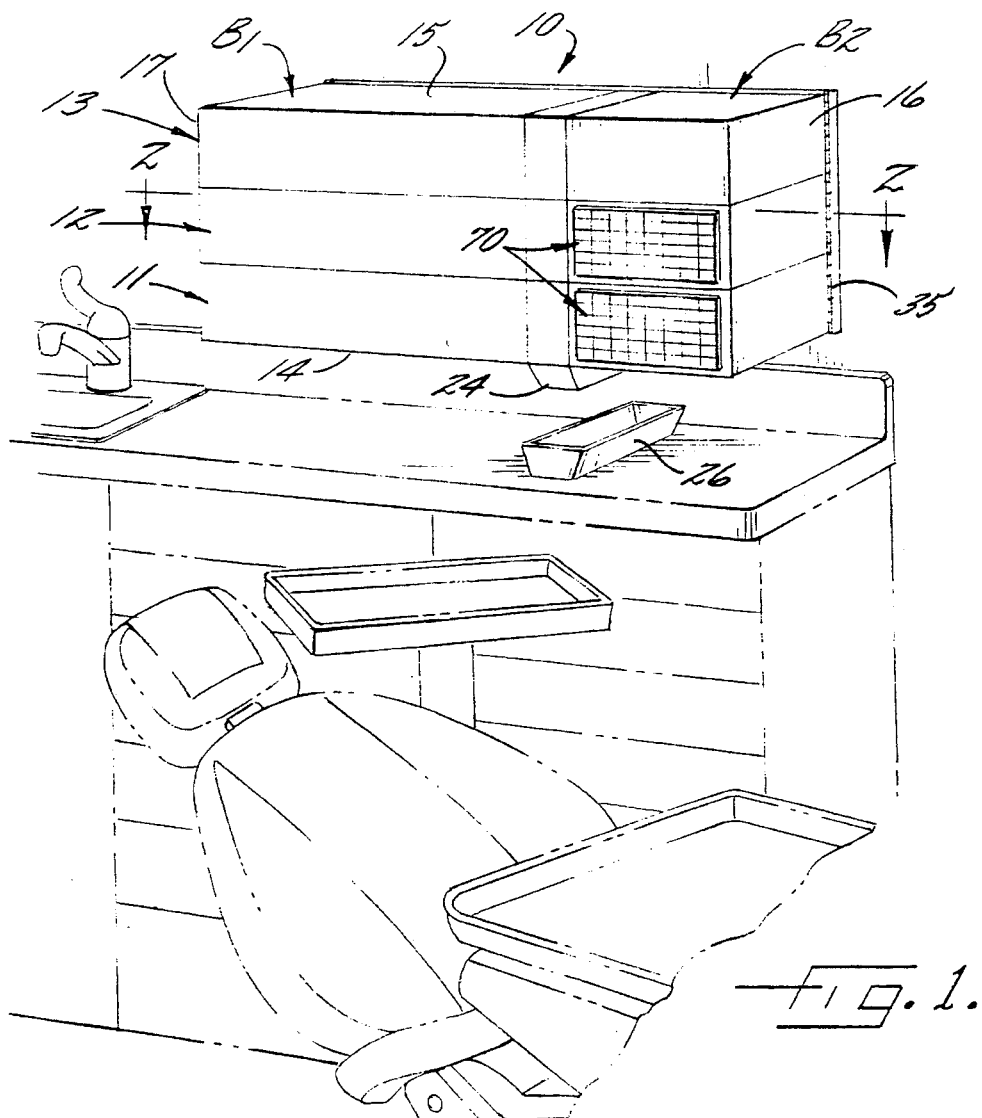
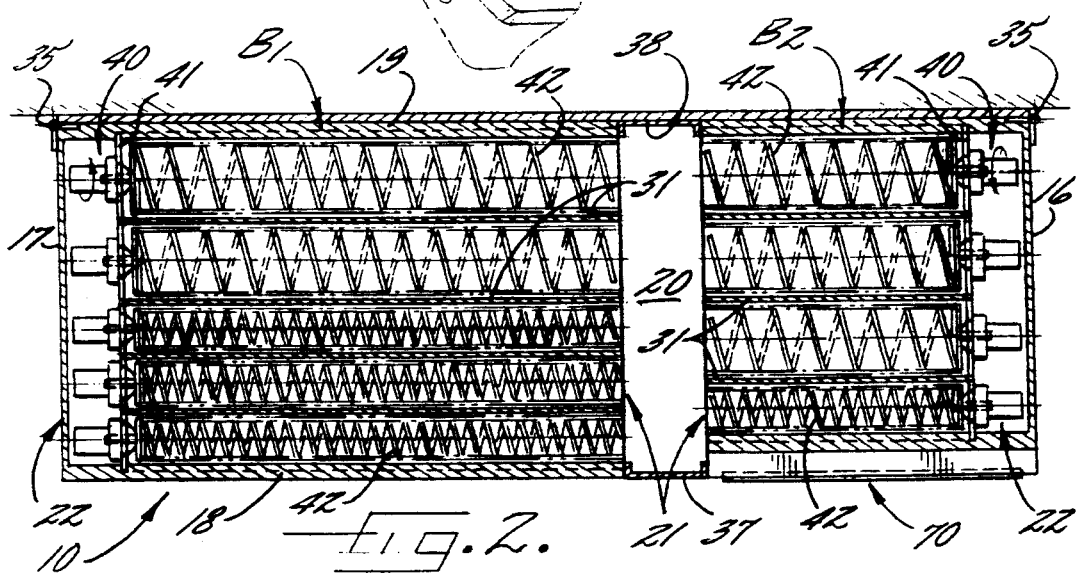

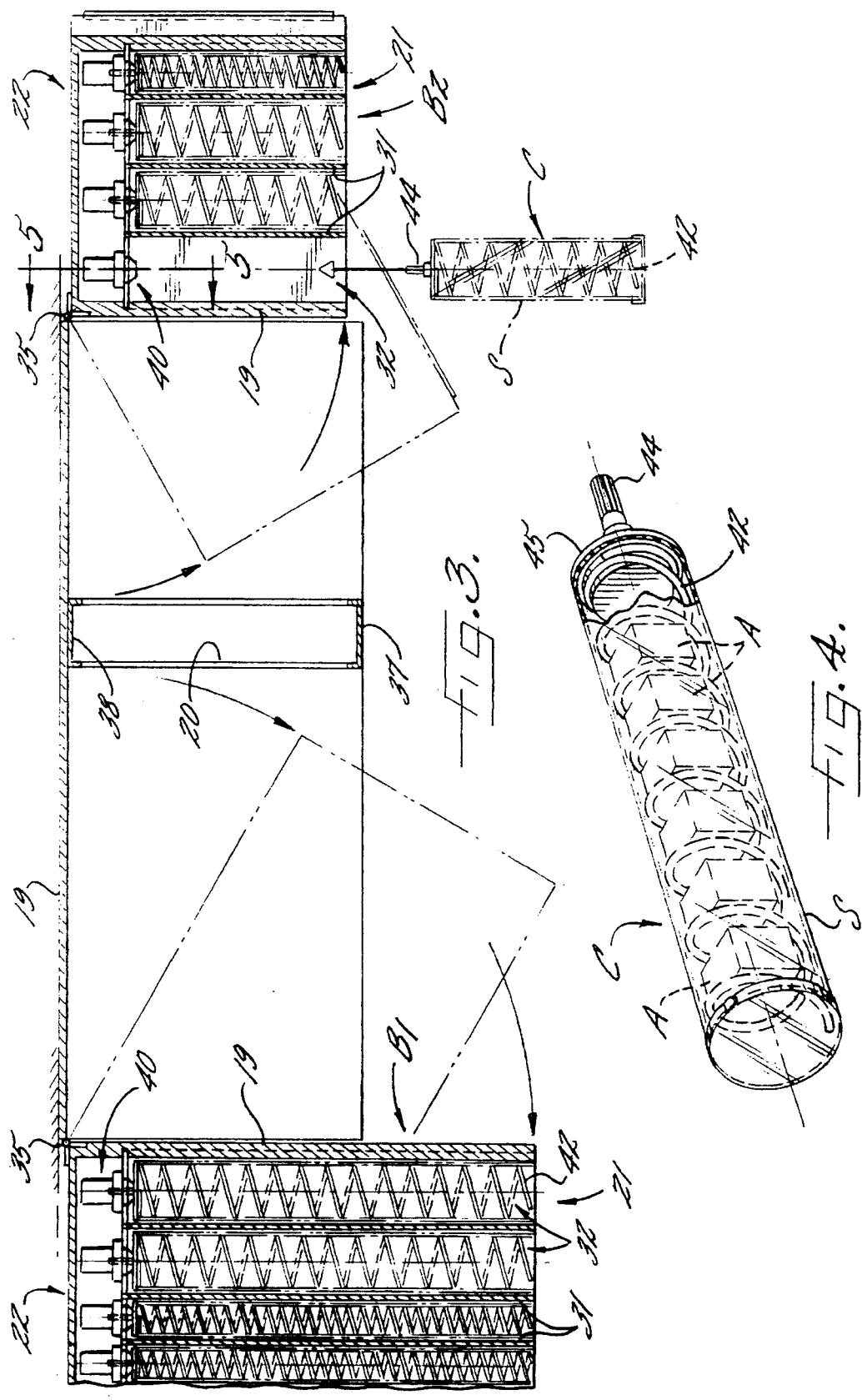

ASEPTIC DISPENSING SYSTEM

BACKGROUND OF THE INVENTION

1. Field of the Invention

The present invention relates to a modular system for providing articles in aseptic condition. More specifically, this invention relates to a device and process for maintaining and delivering articles in an environment where cross-contamination is important.

2. Description of the Prior Art

There are few guidelines for maintaining aseptic conditions in many work environments, such as dentist and doctor offices. Thus, articles such as cotton rolls, disposable drink cups, suction tips, and the like, that come into contact with patient's are not free from pathogenic microorganisms. For example, when a dentist uses a cotton roll, the roll is simply taken from a supply jar or drawer, neither of which is aseptic, and inserted into a patient's mouth.

To maintain articles that are used in treating patients free from pathogenic microorganisms it is necessary to keep the articles away from effected areas such as countertops, non-aseptic storage containers and the like. Numerous procedures, cleansers, storage vessels and other means have been proposed to obtain and maintain aseptic conditions in working environments where cross-contamination is important. To date, however, none have been successful.

SUMMARY OF THE INVENTION

With the foregoing in mind it is an object of this invention to provide a process for maintaining and delivering an article in an aseptic condition to an environment where cross-contamination is important.

Another object of the present invention is to provide a system for maintaining and dispensing articles for dental, medical or like applications in an aseptic environment.

Yet another object of the present invention is to provide a preloaded aseptic cartridge for loading into a modular dispensing system.

An even further object of the present invention is to provide a process for dispensing articles from a preloaded cartridge.

These objects are accomplished by the present invention in which a system for maintaining and dispensing articles for dental, medical or like applications in an aseptic environment is provided. The system includes a cabinet made up of modular units having at least one bank of shelves. Each bank has an open end and a closed end such that the open end is oriented toward a dispensing chute. Each bank contains a plurality of horizontally adjustable shelves laterally disposed in the bank. The shelves are divided by a plurality of vertical dividers to define a series of slots in the shelves. One type of article is stored in and dispensed from each slot.

A dispensing chute is located adjacent the open end of each bank and is adapted to provide gravity feed of an aseptic article. A discharge outlet aids in directing the dispensed article from the chute. The articles are fed toward the dispensing chute by a feeding means such as an auger or tractor feed and the leading article is discharged by gravity. There is provided a plurality of drive means fixed to an interior wall at the closed end of the bank with one drive means being for each slot in the shelves to drive the feed means. The operation of the feed means may be controlled mechanically, electro-mechanically or by a microprocessor or the like to feed articles to the dispensing chute.

The present invention also contemplates a drop-in, preloaded cartridge which includes an auger prepackaged with the articles to be dispensed unwrapped in an aseptic condition so that when inserted into the respective slot the outer wrapping simply has to be removed and the cartridge placed in the slot with the auger operatively connected to the drive means.

The present invention is also directed to a process for maintaining and delivering an article in an environment where cross-contamination is important. The process includes providing a cabinet having at least one bank of shelves having an open end and a closed end such that the open end is oriented toward a dispensing chute. A plurality of horizontally adjustable shelves laterally disposed in each bank of the cabinet is provided. Each shelf is divided by a plurality of vertical dividers to define slots in the shelves for holding articles packaged in an aseptic condition. The process includes placing a prepackaged cartridge into the appropriate slot in operating relationship with the drive means and storing the articles to be dispensed. In the preferred embodiment, the user selects the article desired by simply touching the keypad which activates the feeding means. The articles are fed along the slot toward the open end of the bank to a delivery chute and the leading article is discharged to the user in an aseptic condition.

BRIEF DESCRIPTION OF THE DRAWINGS

Other objects, features and advantages of the present invention will become apparent from the following detailed description when taken in conjunction with the accompanying drawings in which:

FIG. 1 is a perspective view of the modular system of the present invention;

FIG. 2 is a top view of an embodiment of a modular unit of the delivery system of the present invention as shown along line 2—2 of FIG. 1;

FIG. 3 is an exploded partial top view illustrating a modular unit having a pair of banks in outward or loading position;

FIG. 4 is a view of the prepackaged cartridge of a preferred embodiment of the present invention;

DESCRIPTION OF THE PREFERRED EMBODIMENT

Figure 5:
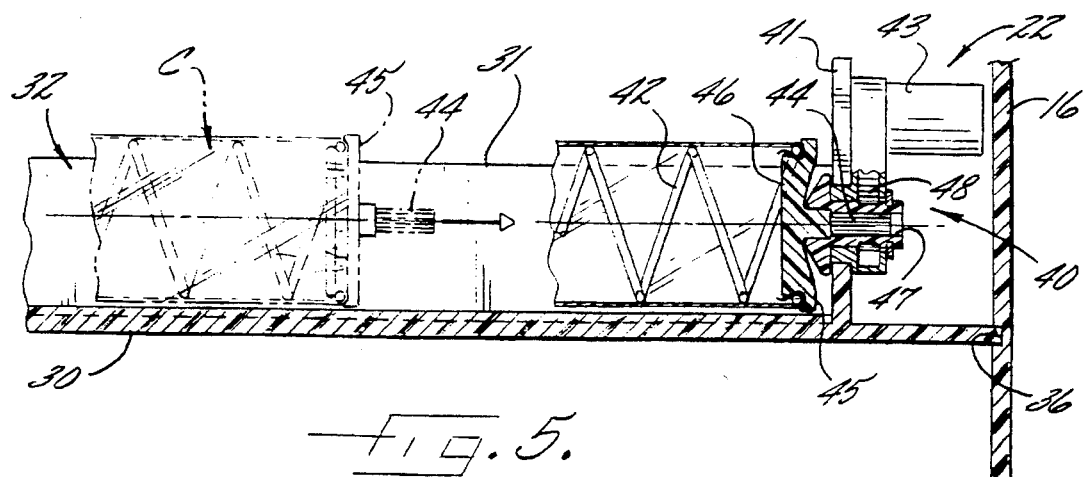
FIG. 5 is a cutaway of a prepackaged cartridge of the present invention positioned in a slot of the dispensing system as shown along line 5—5 of FIG. 3.

Referring now to the drawings, FIG. 1 shows a perspective view of the modular dispensing system 10 for maintaining and dispensing articles for dental, medical or like applications in an aseptic environment of the present invention in which there is shown a bank of cabinets to be mounted to a wall in a dentist's office. In the embodiment of FIG. 1 there is shown a set of three tiers of cabinets 11, 12, and 13. The number of tiers is only limited by the amount of space available and the number of articles to be dispensed. Each cabinet has a bottom 14, a top 15, side walls 16 and 17, a front wall 18 and a rear wall 19. The dispensing system 10 delivers a single article to the user, thus eliminating contamination to the remaining articles. While dispensing the system shown in FIG. 1 is mounted to a wall, it should be understood that the system may be free standing to sit on a counter or on the floor. The free standing system may be made portable so that it may be used in several examination rooms.

As shown more clearly in the embodiment illustrated in FIG. 2, which is representative of one of tiers 11, 12, or 13, each cabinet has two banks B1 and B2 of shelves 30. Each bank is positioned so that it has an open end 21 and a closed end 22 such that the open ends 21 are oriented toward and form the dispensing chute 20. The other sides of dispensing chute 20 are shown in FIG. 2 as front spacer 37 and rear spacer 38.

Figure 6:
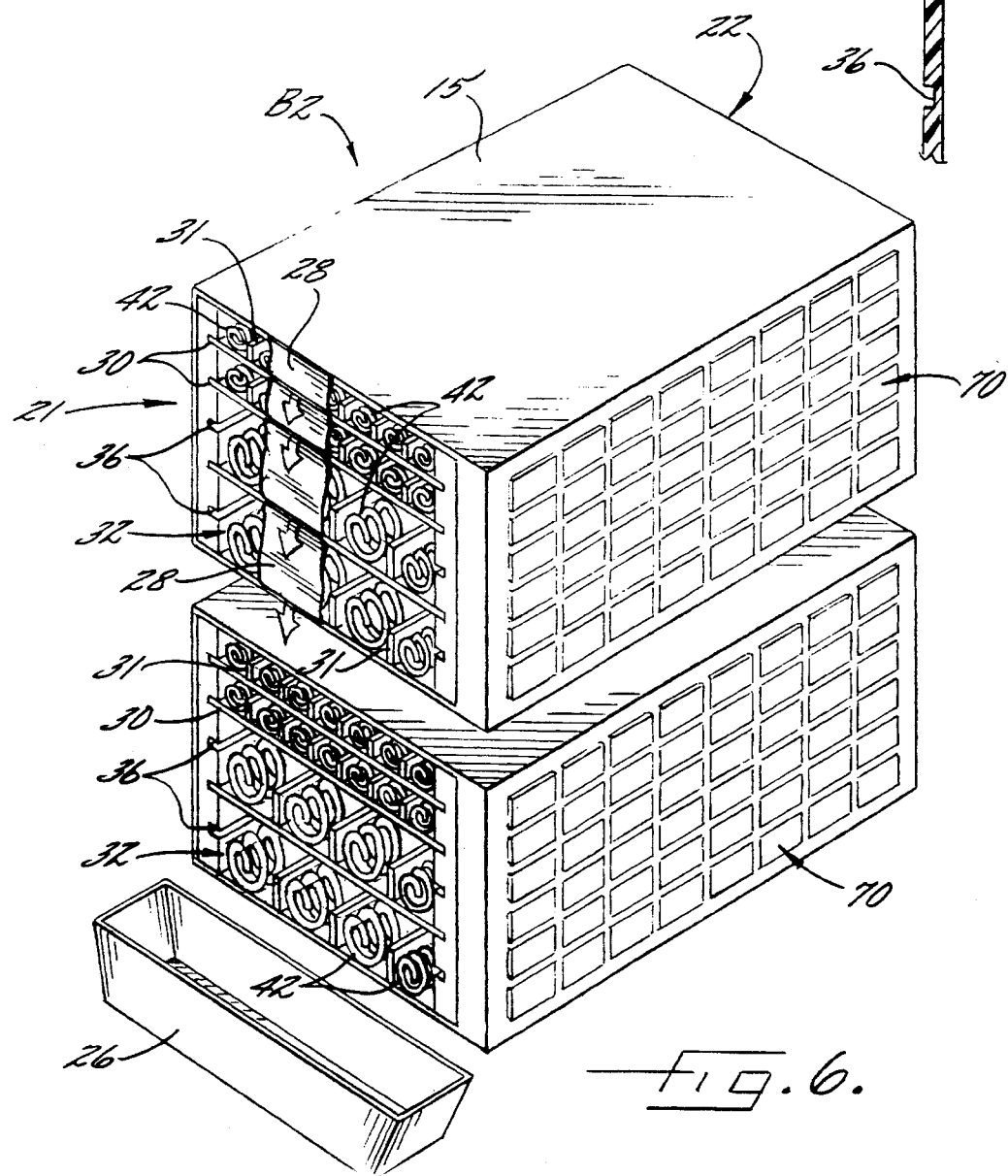
FIG. 6 illustrates a perspective view of the stackable nature of the dispensing system of the present invention.

As shown in FIG. 6, a plurality of horizontally adjustable shelves 30 are laterally disposed in each bank. The shelves 30 are capable of being divided by a plurality of laterally spaced vertical dividers 31 wherein the vertical dividers 31 define a plurality of article feed slots 32 on each shelf for individual articles. The shelves 30 are inserted laterally into the bank at the open end 21 by sliding into shelf slots 36. The shelf slots 36 may be inclined slightly in a downward direction from the closed end to the open end to help minimize potential contamination. The feed slots 32 provide guidance for the feeding means and consequently the vertical dividers 31 are not required to extend from the top of one shelf to the bottom of the next upper shelf. The feed slots 32 may, of course, vary in width. In fact, it is preferred that the vertical dividers only be of sufficient height to provide the guidance for the feeder so as not to interfere with the placement of the horizontally adjustable shelf.

A dispensing chute 20 located adjacent to and formed by the open end of the banks B1 and B2 and adapted to provide gravity feed of an aseptic article into a disposable or reusable, sterilizable tray 26. In the configuration of FIG. 2 where there are banks B1 and B2, the open proximate end of each bank form the boundary of chute 20. As shown in FIG. 2 the chute 20 separates the lateral banks B1 and B2 such that the shelves on one side are shorter than the shelves on the other side to permit articles used less frequently to be placed in the shorter shelves. The shelves 30 are mounted one above another in slots 36 located in the front wall 18 and rear wall 19.

Figure 7:
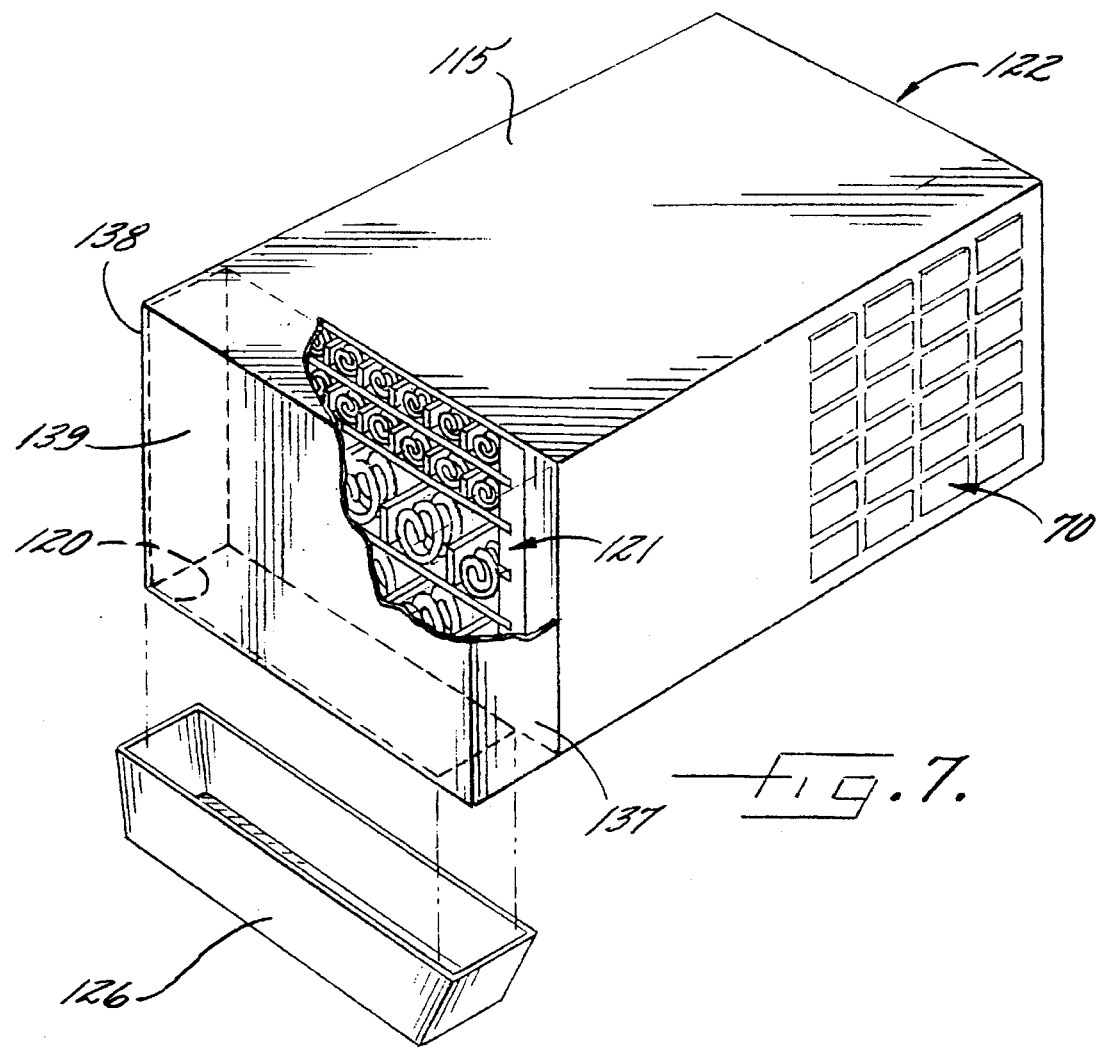
FIG. 7 is a perspective view of an embodiment of the present invention illustrating a single bank of shelves.

In the embodiment shown in FIG. 7, there is a single bank of shelves having an open end 121 and a closed end 122. There is a dispensing chute 120 adjacent the open end 121. The dispensing chute has a front wall 137, a rear wall 138 and an end wall 139. The embodiment of FIG. 7 operates in the same manner as a two bank embodiment wherein the lead article drops downwardly through delivery chute 120 into a delivery tray 126.

Each bank is mounted at its closed end 22 to the rear wall 19 by vertical pivot post 35, as shown in FIGS. 2 and 3 so that the respective bank may swing outwardly about the axis of post 35 so that each shelve may be easily loaded with articles. As shown in FIG. 3, an empty cartridge C is simply removed from its respective slot 32 by disengaging the drive shaft and a fresh preloaded cartridge is inserted.

An article delivered from any one of the shelves drops downwardly through delivery chute 20, through the opening in port 24 (see FIG. 1) into a delivery tray 26 providing a convenient delivery station below the cabinet, from which the article may be taken out in aseptic condition by the user. The mouth of the delivery tray 26 should be at least as large as the opening in port 24 so that the article will always fall into the tray.

As shown in FIG. 6, there may also be a curtain or partition of any suitable material 28 extending over the open end of the shelves. The curtain 28 aids in preventing the hang up of a dispensed article on a lower shelf as the article falls downwardly through the chute 20. The curtain also serves to maintain the bank in an aseptic condition. This closure extends heightwise at the open end of each bank. The height is about one shelf high taking into account the fact that the height between shelves may vary.

The means for feeding the articles toward the dispensing chute may be performed by a variety of means such as the auger 42 shown in FIG. 2 or a tractor feed (not shown). To feed an article to the open end 21 of slot 32 and into dispensing chute 20, a helix auger 42 is provided for each slot. For some articles that need a wide slot for delivery, it has been found desirable to use two helical augers in tandem.

As shown in FIG. 5 the feed means exemplified by helical auger 42 is made operative by drive means 40 fixed to the interior of the closed end 21 of the bank. Each drive means 40 includes a drive motor 43 in communication with the control means. The drive means includes internal gearing 48 for drivably receiving the drive shaft 44 of the helix auger 42 in an axial manner. The drive means 40 is mounted on support wall 41 which is spaced inwardly from the side wall 16 or 17 to provide a space therebetween to receive portions of the drive means 40. The drive means 40 has a female receiving member 47 extending through support wall 41 to operatingly but releasably receive drive shaft 44.

As shown in FIG. 4, each slot 32 of the bank carries an elongated coil 42 with windings extending lengthwise of the slot. Each helix coil 42 being adapted to receive articles A to be dispensed between its convolutions for screw-feeding the article toward the open end 21 and discharging the leading article into the dispensing chute 20 to drop by gravity into tray 26. The elongated helical coil 42 is secured at the rear end to a circular plate 45 including a drive shaft 44 connected to the plate and operatively connected to a drive means 40 and adapted to be angularly driven. The auger may be held in place using a spring lock. The helix augers may, of course, be of differing sizes to better accommodate different sized articles. The driven shaft 44 is fluted or keyed for releasing engagement with the female drive means receiving member 47. In an alternative embodiment, the feed means may be a tractor feed wherein the tractor feed is formed of a circular belt having article holding members.

The delivery of articles to the dispensing chute 20 may be controlled by a variety of means. A preferred control means is shown in FIGS. 1 and 6, as keypad 70 which is provided on the front of each modular unit for each type of article stored in each slot of banks B1 and B2 of the unit. Each key is a pushbutton switch for making a selection from the respective slot. Each pushbutton switch is coded for the appropriate article for ease in making selections of articles. The keypads are connected to the drive means 40 in a conventional manner. The keypad may also be connected to a microprocessor programmed for inventory control. The keypad 70 may have a replaceable clear sheet or film adapted to cover the keypad to help maintain the keypad in an aseptic condition. In another embodiment, the dispensing system is activated by a voice or word recognition system without touching the keypad. The voice activated system may be used with either a wall mounted system or a portable system. The portable system is preferably battery powered, and thus can easily accommodate a voice activated system. There may be included as part of the control means a light for each article warning that few articles remain in the slot and thus reloads will soon be required.

The present invention further contemplates a drop-in, preloaded cartridge C of prepackaged articles A in a helical auger 42, such that a cartridge containing the articles is inserted in each slot 32. The helical auger is wrapped in a sleeve S designed to accommodate the shape of the articles. The loaded cartridge may be shipped to the dispensing location and loaded directly into a dispenser. The sleeve can take on a number of different shapes dependent upon the shape of the article to be dispensed.

Once the auger encapsulated in the sleeve, i.e., the preloaded cartridge, reaches the location of the system, the protective wrapping is removed from the cartridge. In one form, see FIG. 4, the protective sleeve S remains around the auger during use and a wrap covering the front opening of the sleeve is removed. The cartridge is inserted into the appropriate slot of the system. The membrane separator is then removed from the auger.

Once at the dispensing location, the empty cartridge is removed and the full cartridge is loaded into the appropriate slot 32 of FIG. 3. Upon selection of the correct soft touch keypad 70, the auger rotates and feeds the lead article into the dispensing chute 20.

When it is time to reload the dispenser with new or restocked articles, the "empty" auger is removed from the slot of the shelve, the sleeve from the cartridge having products disposed within each compartment of the spiral auger is removed, and the replacement auger with the articles disposed therein is placed in the slot on the shelf of the dispensing machine. The empty auger may then either be discarded or returned to the packager.

There are several different embodiments for the helical auger, including an open auger configuration as shown in FIG. 4, a split auger having a divider (not shown), or a solid auger for use with small articles (not shown).

The open auger is preferably a wire-type helical-shaped auger. Once the items have been inserted in the slots defined by the auger, a sleeve or wrapper S is placed over the auger having the products disposed for shipment in an aseptic condition.

The axis of the solid auger is not hollow, but rather, is solid and is particularly useful for small items. The solid auger also has a horizontal slot through the entire length of the axis of the auger into which a removable separation membrane may be inserted during the packaging process in order to maintain a single unit of the article in the lower half of each slot during shipping. This embodiment prevents intermingling of the units of the product during shipping.

The dispensing system may also be designed to include the adaption of automatic epoxy and filling material mixers as well as an automatic floss dispenser. These additions may be connected to the bottom of the cabinet in the case of a wall mounted unit or the top in the case of a floor mounted unit.

The present invention also includes a process for maintaining and delivering an article in an environment where cross-contamination is important comprising the steps of providing a cabinet having at least one bank of shelves for holding and storing the articles to be dispensed. Each bank has an open end 21 and a closed end 22 such that the open end 21 is oriented toward a dispensing chute 20. The process further includes providing a plurality of shelves 30 laterally disposed in the bank wherein the shelves are divided by a plurality of vertical dividers 31 defining slots 32 in the shelves for articles in an aseptic condition. The articles to be dispensed are stored on the shelves until needed.

When an article is needed, the user signals the system by pressing the proper keypad to activate the feeding means, e.g., auger, to move the article along the slot toward the open end of the bank to the delivery chutes and discharging the leading article to the user. The auger is turned or driven by a motor. The turning action of the auger causes the articles to travel the length of the slot, one rotation at a time. As a result the auger does not move laterally.

The process also includes the step of loading a fresh cartridge C into the appropriate slot in the cabinet. The process further comprises controlling the delivery of said article through selectively controlling the delivery of the article by providing means for controlling which include a processor means for automatically delivering the article.

Also, the process includes defining at least one or more articles to be delivered using a keyboard. Another embodiment includes maintaining and/or transporting data on delivery in one or more dispensers to a central inventory control.

The present invention makes possible the maintaining and dispensing of a large number of individual articles within a relatively small area. As can be seen, the articles are maintained and dispensed without contaminating any other articles or surfaces. The articles are easily accessible to the user since all the user needs to do is to touch the appropriate keypad. Removal of one or more articles will automatically cause similar articles to be fed into the leading position until such time as all the articles in a particular slot are exhausted. As described, the articles are easily replenished using the preloaded cartridge described herein. Suitable dimensions for any given moduolar unit will vary, of course, with the environment in which it is to be utilized.

While the preferred embodiments of this invention have been illustrated in detail, it should be readily apparent to those skilled in the art that other embodiments may be conceived and fabricated without departing from the spirit and scope of this invention.

What is claimed is:

1. A modular system for maintaining and dispensing articles for dental, medical or like applications in an aseptic environment, said system comprising:

a cabinet having a bank of shelves, said bank having an open end and a closed end;

a dispensing chute adjacent the open end of said bank adapted to provide gravity feed of an article maintained in an aseptic condition;

a plurality of shelves laterally disposed in said bank of said cabinet, said shelves being divided by a plurality of vertical dividers wherein said vertical dividers define article feed slots in the shelves to thereby store and maintain said articles in an aseptic condition;

a plurality of drive means positioned at the interior of the closed end of said bank, each drive means being mounted to a support wall located interiorly of the closed end of the bank and adjacent each of said slots in the shelves;

means for feeding said articles in an aseptic condition toward said dispensing chute and discharging the leading article to drop by gravity, said feeding means being detachably mounted to said drive means; and means for controlling the delivery of articles in an aseptic condition to the dispensing chute.

2. The system for maintaining and dispensing articles for dental, medical or like applications in an aseptic environment according to claim 1 further comprising said cabinet comprising a first bank and a second bank, the open end of each of said banks oriented toward each other in such manner that the open end of each bank faces said dispensing chute.

3. The system for maintaining and dispensing articles for dental, medical or like applications in an aseptic environment according to claim 1 further comprising a tier of at least two cabinets.

4. The system for maintaining and dispensing articles for dental, medical or like applications in an aseptic environment according to claim 1 further comprising means for mounting each of said banks to a vertical pivot post located at the closed distal end of the rear wall so that the respective bank may swing outwardly about the axis of said post so that each slot may be easily loaded with articles to be maintained in an aseptic condition.

5. The system for maintaining and dispensing articles for dental, medical or like applications in an aseptic environment according to claim 1 wherein said means for feeding further comprises in combination a plurality of removable auger feed contained with a protective sleeve, thereby maintaining said articles in an aseptic condition.

6. The system for maintaining and dispensing articles for dental, medical or like applications in an aseptic environment according to claim 5 wherein said auger is a solid auger.

7. The system for maintaining and dispensing articles for dental, medical or like applications in an aseptic environment according to claim 1 wherein said control means is a keypad having a plurality of keys such that one key is associated with one slot in one of the shelves in one of the banks of shelves, said keypad located on the outer surface of said cabinet; said keypad further comprising a clear replaceable film adapted to cover said keypad, thereby maintaining keyboard in an aseptic condition.

8. The system for maintaining and dispensing articles for dental, medical or like applications in an aseptic environment according to claim 1 wherein said shelves are horizontally adjustable.

9. The system for maintaining and dispensing articles for dental, medical or like applications in an aseptic environment according to claim 1 wherein said dispensing chute further comprises a curtain extending over said open end of said bank of shelves thereby maintaining said articles in an aseptic condition.

10. The system for maintaining and dispensing articles for dental, medical or like applications in an aseptic environment according to claim 1 wherein said shelves being inclined in a downward direction from the closed end to the open end thereby maintaining said articles in an aseptic condition.

11. A system for maintaining and dispensing articles for dental, medical or like applications in an aseptic environment, said system comprising:

a cabinet having two banks of shelves, said banks having open ends and closed ends such that each open end is oriented toward a central dispensing chute;

a plurality of horizontally adjustable shelves laterally disposed in said bank of said cabinet, said shelves being divided by a plurality of vertical dividing means wherein said vertical dividing means define article feed slots in the shelves to thereby store and maintain said articles in an aseptic condition;

said dispensing chute located adjacent the open end of said banks adapted to provide gravity feed of an article maintained in an aseptic condition;

a plurality of drive means fixed to the interior of the closed end of said bank, one drive means being fixed to the interior wall of the closed end of the bank adjacent each of said slots in the shelves;

auger means disposed longitudinally within said feed slot being operatively and detachably connected to said drive means for feeding said articles in an aseptic condition toward said dispensing chute and discharging the leading article to said chute to drop by gravity; and means for controlling the delivery of articles in an aseptic condition to the dispensing chute.

12. The system for maintaining and dispensing articles for dental, medical or like applications in an aseptic environment according to claim 11 further comprising a tier of at least two cabinets.

13. The system for maintaining and dispensing articles for dental, medical or like applications in an aseptic environment according to claim 11 wherein said auger is a solid auger.

14. The system for maintaining and dispensing articles for dental, medical or like applications in an aseptic environment according to claim 11 wherein said means for feeding further comprises in combination a removable auger feed contained within a protective sleeve, thereby maintaining said articles in an aseptic condition.

15. The system for maintaining and dispensing articles for dental, medical or like applications in an aseptic environment according to claim 11 wherein said control means is a keypad having a plurality of keys such that one key is associated with one slot in one of the shelves in one of the banks of shelves, said keypad located on the outer surface of said cabinet; said keypad further comprising a clear replaceable film or sheet adapted to cover said keypad, thereby maintaining an aseptic condition.

16. The system for maintaining and dispensing articles for dental, medical or like applications in an aseptic environment according to claim 11 wherein said dispensing chute further comprises a curtain extending over said open end of said bank of shelves thereby maintaining said articles in an aseptic condition.

17. The system for maintaining and dispensing articles for dental, medical or like applications in an aseptic environment according to claim 11 wherein said shelves being inclined in a downward direction from the closed end to the open end.

18. A modular system for maintaining and dispensing articles for dental, medical or like applications in an aseptic environment, said system comprising:

a cabinet having a bank of shelves, said bank having an open end and a closed end;

a dispensing chute adjacent the open end of said bank adapted to provide gravity feed of an article maintained in an aseptic condition, said dispensing chute further comprises a curtain extending over said open end of said bank of shelves thereby maintaining said articles in an aseptic condition;

a plurality of downwardly inclined shelves laterally disposed in said bank of said cabinet, said shelves being divided by a plurality of vertical dividers wherein said vertical dividers define feed slots in the shelves for receiving a cartridge filled with articles in an aseptic condition to be maintained and dispensed in an aseptic condition;

said cartridge comprising a detachable auger having an elongated helical coil with windings secured at a rear end to a circular plate including a drive shaft connected to said plate and operatively connectable to a drive unit and adapted to be angularly driven, said helical coil having sufficient spacing to receive an article between said windings, wherein said article is to be maintained in an aseptic condition, and said rear end means adapted to be angularly driven;

a plurality of drive means positioned at the interior of the closed end of said bank, each drive means being mounted to a support wall located interiorly of the closed end of the bank and adjacent each of said slots in the shelves;

means for feeding said articles in an aseptic condition toward said dispensing chute and discharging the leading article to drop by gravity, said means for feeding further comprises a removable auger feed contained within a protective sleeve; and means for controlling the delivery of articles in an aseptic condition to the dispensing chute, said control means is a keypad having a plurality of keys such that one key is associated with one slot in one of the shelves in one of the banks of shelves, said keypad located on the outer surface of said cabinet;said keypad further comprising a clear replaceable film or sheet adapted to cover said keypad, thereby maintaining an aseptic condition.

19. A process for maintaining and delivering an article in an environment where cross-contamination is important comprising the steps of:

providing a cabinet having at least one bank of shelves, said bank having an open proximal end and a closed distal end such that the open proximal end is oriented toward a dispensing chute;

providing a plurality of shelves laterally disposed in said bank of said cabinet, said shelves being divided by a plurality of vertical dividing means wherein said vertical dividing means defines feed slots in the shelves for guiding said articles and maintaining in an aseptic condition;

placing a cartridge of said articles in an aseptic condition in said slots said cartridge comprising an auger having an elongated helical coil with windings secured at a rear end to a plate including a drive shaft connected to said plate and operatively connectable to a drive means and adapted to be angularly driven;

storing said cartridge of articles in an aseptic condition to be dispensed on one of said shelves;

feeding said articles in an aseptic condition along said slot toward the open proximal end of said bank to a delivery chute; and discharging the leading article to the user in an aseptic condition.

20. The process for maintaining and delivering a product in an environment where cross-contamination is important according to claim 19 further comprising controlling the delivery of said article.

21. The process for maintaining and delivering a product in an environment where cross-contamination is important according to claim 19 further comprising selectively controlling the delivery of said article by providing means for controlling further including a processor means for automatically delivering the article.

22. The process for maintaining and delivering a product in an environment where cross-contamination is important according to claim 19 further comprising defining at least one or more articles to be delivered using a keyboard.

23. The process for maintaining and delivering a product in an environment where cross-contamination is important according to claim 19 further comprising transporting data on delivery in one or more dispensers in said system.

24. The process for maintaining and delivering a product in an environment where cross-contamination is important according to claim 19 further comprising the step of loading a cartridge containing said articles and a feeding means into said slots.

25. The process for maintaining and delivering a product in an environment where cross-contamination is important according to claim 19 further comprising defining at least one or more articles to be delivered using a keypad and maintaining said keypad in an aseptic condition by covering said keypad with a clear replaceable film.

26. The process for maintaining and delivering a product in an environment where cross-contamination is important according to claim 19 further comprising the step of lining said dispensing chute with a curtain extending over said open end of said bank of shelves to maintain said articles in an aseptic condition.

27. The process for maintaining and delivering a product in an environment where cross-contamination is important according to claim 24 further comprising the step of encircling said cartridge in a protective sleeve for storing and maintaining said article in an aseptic condition.

28. A process for maintaining and delivering an article in an environment where cross-contamination is important comprising the steps of:

providing a cabinet having at least one bank of shelves, said bank having an open proximal end and a closed distal end such that the open proximal end is oriented toward a dispensing chute;

providing a plurality of shelves laterally disposed in said bank of said cabinet, said shelves being divided by a plurality of vertical dividing means wherein said vertical dividing means defines slots in the shelves for guiding said articles and maintaining an aseptic condition;

placing a preloaded cartridge of said articles in an aseptic condition in said slots wherein said cartridge comprises an auger having an elongated helical coil with windings secured at a rear end to a circular plate including a drive shaft connected to said plate and operatively connectable to a drive unit and adapted to be angularly driven, said helical coil having sufficient spacing to receive an article between said windings, said rear end means being adapted to be angularly driven; and a protective sleeve encircling said auger containing articles in an aseptic condition to be dispensed;

storing said cartridge of articles in an aseptic condition to be dispensed on one of said shelves;

feeding said articles in an aseptic condition along said slot toward the open proximal end of said bank to a delivery chute; and discharging the leading article to the user in an aseptic condition.

* * * * *

UNITED STATES PATENT AND TRADEMARK OFFICE
CERTIFICATE OF CORRECTION

PATENT NO. : 5,509,573  Page 1 of 2
DATED : April 23, 1996
INVENTOR(S) : William J. Campoli It is certified that error appears in the above-identified patent and that said Letters Patent is hereby corrected as shown below:

Column 1, line 16, delete "patient's" insert -- patients --.

Column 1, line 22, delete "effected" insert -- affected --.

Column 2, last line, delete "dispensing the" insert -- the dispensing --.

Column 3, line 25, delete "shelve" insert -- shelf --.

Column 3, line 30, after "20" insert -- is --.

Column 3, line 54, delete "shelve" insert -- shelf --.

Column 4, line 2, delete "shelve" insert -- shelf --.

Column 4, line 29, delete "being" insert -- is --.

Column 4, line 39, delete "driven" insert -- drive --.

Column 6, line 28, delete "moduolar" insert -- modular --.

Column 7, line 30, before "keyboard" insert -- the --.

Column 9, line 16, after "cabinet;" insert a space.

UNITED STATES PATENT AND TRADEMARK OFFICE
CERTIFICATE OF CORRECTION

PATENT NO. : 5,509,573
DATED : April 23, 1996
INVENTOR(S) : William J. Campoli

It is certified that error appears in the above-indentified patent and that said Letters Patent is hereby corrected as shown below:

Column 9, line 35, after "slots" insert a comma (,).

Signed and Sealed this

Nineteenth Day of November, 1996

*Attest:*

BRUCE LEHMAN

*Attesting Officer*     *Commissioner of Patents and Trademarks*